US008119408B2

(12) United States Patent
Norman

(10) Patent No.: US 8,119,408 B2
(45) Date of Patent: Feb. 21, 2012

(54) ENCODED CARRIER AND A METHOD OF MONITORING AN ENCODED CARRIER

(75) Inventor: Carl Edward Norman, Cambridge (GB)

(73) Assignee: Kabushiki Kaisha Toshiba, Tokyo (JP)

( * ) Notice: Subject to any disclaimer, the term of this patent is extended or adjusted under 35 U.S.C. 154(b) by 1351 days.

(21) Appl. No.: 11/090,073

(22) Filed: Mar. 28, 2005

(65) Prior Publication Data

US 2005/0221361 A1    Oct. 6, 2005

(30) Foreign Application Priority Data

Mar. 31, 2004 (GB) .................................. 0407350.8

(51) Int. Cl.
*G01N 21/01* (2006.01)
*G01N 21/45* (2006.01)
*G01N 37/00* (2006.01)

(52) U.S. Cl. ....... 436/56; 422/82.05; 422/400; 422/402; 436/164; 436/518; 436/524; 436/525; 436/527

(58) Field of Classification Search .............. 422/56–57, 422/82.05–82.09, 82.11, 400–402, 425, 500; 436/56, 518, 524–527, 164
See application file for complete search history.

(56) References Cited

U.S. PATENT DOCUMENTS

| | | | | |
|---|---|---|---|---|
| 3,652,159 A | * | 3/1972 | Lietar ........................... | 356/4.04 |
| 5,620,850 A | * | 4/1997 | Bamdad et al. ............... | 530/300 |
| 5,841,128 A | * | 11/1998 | Shibuya et al. ............ | 250/208.1 |
| 6,096,496 A | * | 8/2000 | Frankel ............................ | 506/31 |
| 6,262,419 B1 | * | 7/2001 | Huth-Fehre et al. ........ | 250/341.8 |
| 6,458,583 B1 | | 10/2002 | Bruhn et al. | |
| 6,905,885 B2 | * | 6/2005 | Colston et al. ................. | 436/518 |
| 7,829,326 B2 | * | 11/2010 | Norman ........................ | 435/287.1 |
| 2001/0051714 A1 | * | 12/2001 | Chen et al. .................... | 536/24.3 |
| 2002/0084329 A1 | * | 7/2002 | Kaye et al. ............... | 235/462.01 |
| 2002/0102743 A1 | * | 8/2002 | Majumdar et al. ............ | 436/518 |
| 2002/0137059 A1 | * | 9/2002 | Wu et al. ............................ | 435/6 |
| 2002/0182629 A1 | | 12/2002 | Rich | |
| 2002/0187501 A1 | * | 12/2002 | Huang et al. ....................... | 435/6 |
| 2003/0008323 A1 | * | 1/2003 | Ravkin et al. .................. | 435/7.1 |
| 2003/0027351 A1 | * | 2/2003 | Manalis et al. ................ | 436/165 |

(Continued)

FOREIGN PATENT DOCUMENTS

EP    1 415 715 A1    5/2004

(Continued)

OTHER PUBLICATIONS

Xu, W. et al, Nippon Kikai Gakkai Ronbunshu, A-hen 1996, 62, 2757-2763.*

(Continued)

*Primary Examiner* — Arlen Soderquist
(74) *Attorney, Agent, or Firm* — Oblon, Spivak, McClelland, Maier & Neustadt, L.L.P.

(57) ABSTRACT

A method of tracking target molecules produced in a chemical reaction the method comprising providing a reaction region on a carrier, the carrier being arranged such that the target molecules react with the reaction region causing flexion of the carrier introducing the carrier to target molecules; illuminating the carrier with radiation such that radiation reflected from or transmitted through the flexed carrier forms a caustic optical feature; and measuring the position of the caustic to determine if the reaction region has reacted with the target molecules.

10 Claims, 13 Drawing Sheets

U.S. PATENT DOCUMENTS

| | | | |
|---|---|---|---|
| 2003/0082587 A1* | 5/2003 | Seul et al. | 435/6 |
| 2003/0129654 A1* | 7/2003 | Ravkin et al. | 435/7.1 |
| 2003/0134330 A1* | 7/2003 | Ravkin et al. | 435/7.1 |
| 2003/0203390 A1* | 10/2003 | Kaye et al. | 435/6 |
| 2004/0075907 A1* | 4/2004 | Moon et al. | 359/566 |
| 2004/0096911 A1* | 5/2004 | Siniaguine et al. | 435/7.1 |
| 2004/0125424 A1* | 7/2004 | Moon et al. | 359/2 |
| 2004/0126875 A1* | 7/2004 | Putnam et al. | 435/287.2 |
| 2004/0132005 A1* | 7/2004 | Hsu et al. | 435/4 |
| 2004/0152129 A1* | 8/2004 | Garey et al. | 435/7.1 |
| 2004/0152211 A1* | 8/2004 | Majumdar et al. | 436/518 |
| 2005/0079635 A1* | 4/2005 | Norman | 436/514 |
| 2006/0072177 A1* | 4/2006 | Putnam et al. | 359/2 |

FOREIGN PATENT DOCUMENTS

| | | | |
|---|---|---|---|
| GB | 2334347 | * | 8/1999 |
| GB | 2349641 | * | 11/2000 |
| WO | WO 99/31486 | | 6/1999 |
| WO | WO 01/36958 A1 | | 5/2001 |
| WO | WO 01/51207 A1 | | 7/2001 |
| WO | 02/083292 | * | 10/2002 |

OTHER PUBLICATIONS

Xiao, X.-Y. et al, Angewandte Chemie, International Edition in English 1997, 36, 780-782.*

Chang, R. S. et al, Journal of Biotechnology 2004, 108, 1-9.*

* cited by examiner

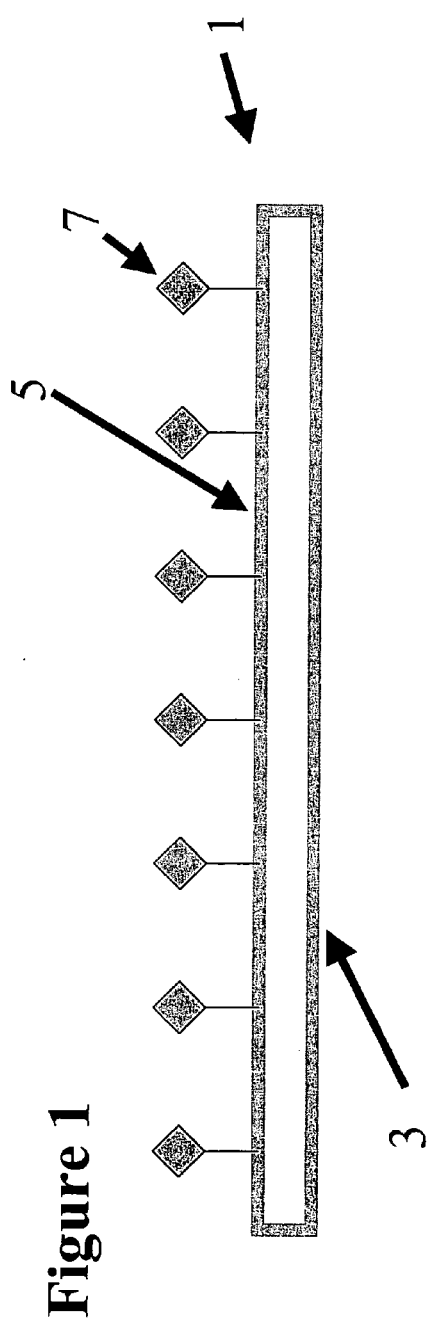
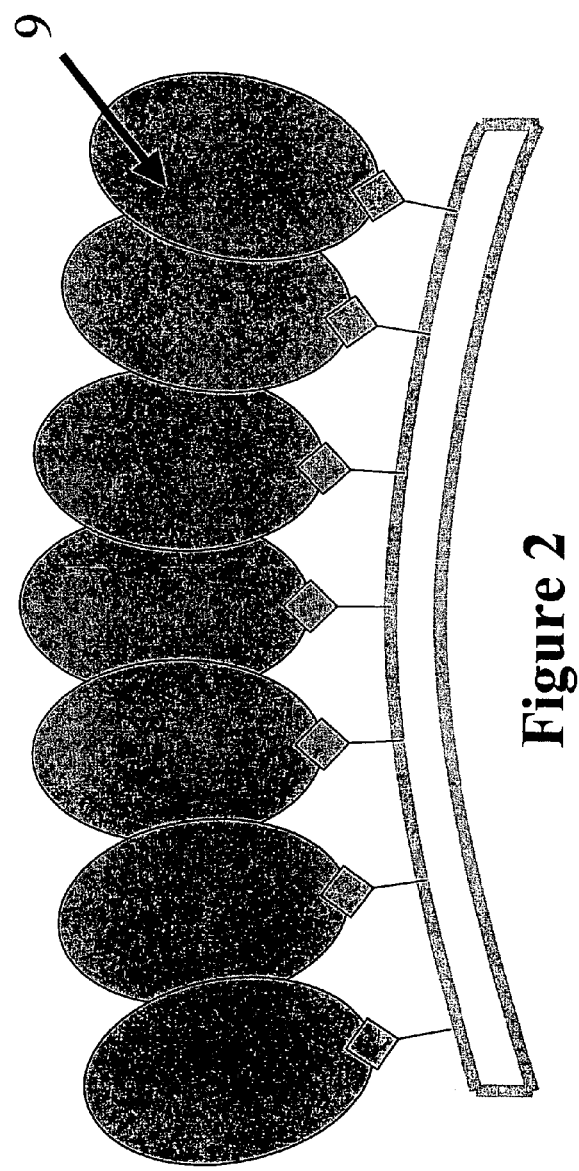

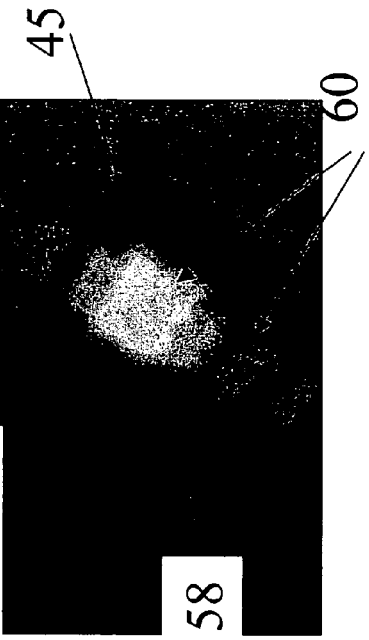
Fig 8b
Fig 8c
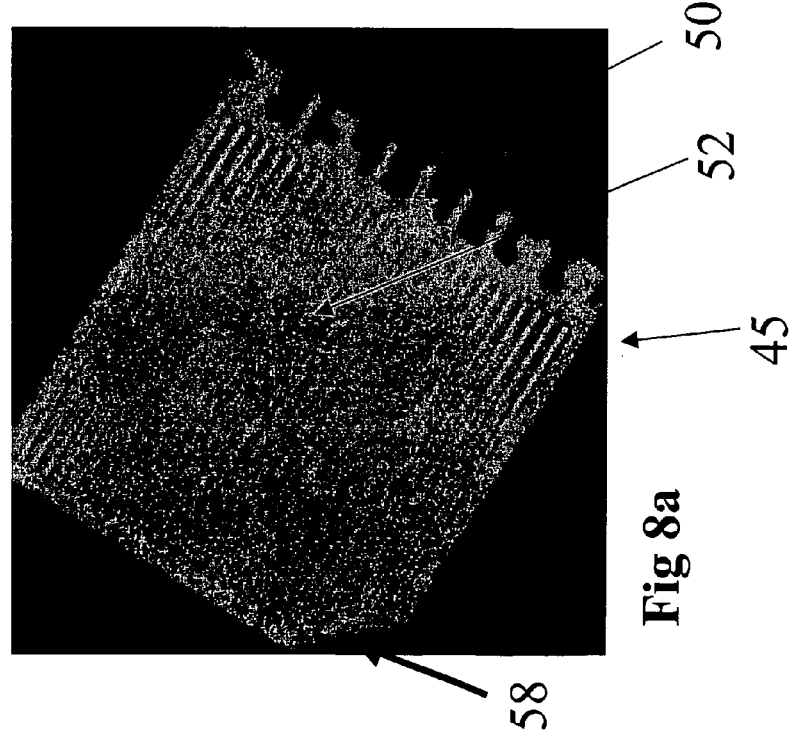
Fig 8a
Figure 8

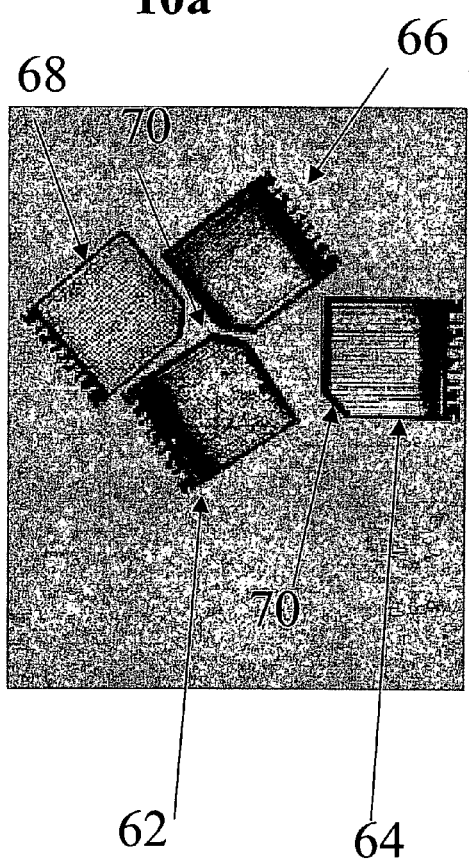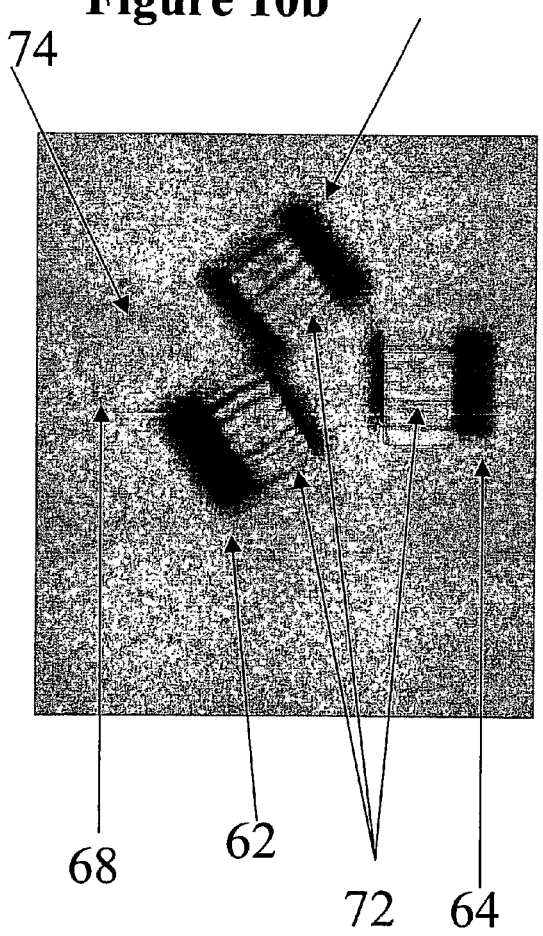
Figure 10a
Figure 10b ns and in particular to the field of encoded carriers prima-
ENCODED CARRIER AND A METHOD OF MONITORING AN ENCODED CARRIER The present invention relates to methods of detecting reactions and in particular to the field of encoded carriers primarily for use in analysing a particular chemical species or to monitoring molecular reactions.

There has always been a need to be able to quickly and efficiently monitor reactions between different chemicals in order to both identify unknown molecules and to study the reactions of both known and unknown molecules. This need has become all the more acute with the substantial and numerous discoveries being made in the biotechnology field.

DNA has the capacity to "hybridise", in other words, a single strand of DNA is capable of pairing to its complementary single strand but not pairing to an unrelated sequence. Using this technique it is possible to identify and monitor the reactions of an unknown strand of DNA by attempting to hybridise it with known DNA strands.

Currently, there are a number of methods for performing this analysis. In one of the known methods, a known molecule or "probe" is reacted with an unknown molecule or "target", to analyse the target molecule. The probe is tethered to a stable material and is generally labelled with a radioactive isotope or fluorophore that can be detected after hybridisation takes place.

WO00/16893 describes a system where probes are attached to a plurality of different coded carriers. The target molecules are tagged and are introduced to the probes with the coded carriers.

GBP2306484 relates to a technique similar to WO00/16893 which uses coded carriers in order to monitor reactions between polymers and the like.

In a further method, a so-called DNA microarray, "spots" of different probe molecules are attached to an inert material such as glass or nylon which are then exposed to labelled target molecules.

Although effective, the above methods are label or tag based methods which require the awkward process of attaching a fluorescent tag molecule to either the probe or the target molecule which can be difficult and time consuming to implement. Interest is now growing in non-tag based methods A different class of devices are based on the use of a tethered cantilever such as described in U.S. Pat. No. 6,289,717. Such devices comprise a micro-cantilever structure, the cantilever having one of its surfaces coated with a material such that the amount of absorption of molecules (from the reaction under analysis) is different on opposing surfaces of the cantilever. The small stress differences between the two surfaces causes bending of the cantilever which is then read by, for example, piezo-electric or laser deflection means.

Such cantilever devices are limited in that they are difficult to fabricate and a system based on such a device cannot easily be re-configured to detect new molecular species without fabricating a new cantilever structure. The detection methods for such devices can also be difficult to operate.

It is therefore an object of the present invention to provide a method of tracking a chemical reaction and to provide a carrier probe suitable for use with said method which substantially overcomes or mitigates problems associated with prior art methods and devices.

Accordingly the invention provides for a method of determining the presence of a target molecule, the method comprising providing a reaction region on a carrier, the carrier being substantially planar and arranged such that the target molecules react with the reaction region causing flexion of the carrier introducing the carrier to target molecules;

illuminating the carrier with radiation; and analysing radiation reflected from or transmitted through the carrier for the presence of a caustic optical feature in order to determine if the reaction region has reacted with the target molecules.

In a further aspect of the present invention there is provided a method of tracking target molecules produced in a chemical reaction the method comprising:

providing a reaction region on a carrier, the carrier being arranged such that the target molecules react with the reaction region causing flexion of the carrier introducing the carrier to target molecules;

illuminating the carrier with radiation such that radiation reflected from or transmitted through the flexed carrier forms a caustic optical feature; and measuring the position of the caustic to determine if the reaction region has reacted with the target molecules.

Caustics were first introduced and studied by Tschirnhausen in 1682. Other contributors are Huygens, Quetelet, Lagrange, and Cayley. A caustic is generally described as a curve to which the ray of light, reflected or refracted by another curve, are tangents, the reflecting or refracting curve and the luminous point being in one plane.

Optical caustics are points, curves or surfaces of anomalously bright light and are often observed on the surface of liquids in cups—the caustic is the observed double arc of reflected light on the liquid's surface. Caustics may also appear as a web of wavy lines on the floor of a swimming pool or reflected on the hull of a boat. Caustics can be caused by reflection, as in the "coffee cup" caustic, or by refraction, as in the swimming pool example. Caustics caused by reflection are called catacaustics and those created by refraction/diffraction, diacaustics.

In the case of the carrier used in the first aspect of the present invention selective binding of a target molecule to the carrier causes the carrier to bend. The surface of the carrier is then illuminated with radiation and analysed for the presence of a caustic optical feature. If the carrier is substantially flat in profile then no caustic optical features will be present. Therefore the method according to this first aspect of the present invention allows a simple determination to be made indicating whether a reaction with a target species has taken place.

For a carrier that was initially flat in profile, subsequently observing the presence of a caustic indicates that a reaction with the target species has taken place.

For a carrier that was initially curved in profile then the disappearance of a previously visible caustic optical feature also indicates that a reaction with the target species has taken place.

The illuminating radiation may be white light comprising a plurality of distinct wavelengths or a single wavelength. The radiation may be in the range from ultra-violet through to near infra-red, e.g. from around 200 nm to 2 μm.

As the reaction between the target species and the carrier progresses the carrier deflection will increase. The position of a caustic optical feature will depend on the geometry of the reflecting or transmitting curve and so, according to the second aspect of the present invention, measuring the position of the caustic produced by the carrier also allows a determination of whether the target molecules have reacted with the probe molecules of the carrier.

The reaction kinetics may also be monitored in the second aspect of the present invention since the measured position of a caustic will change dependent on the number of target molecules which have reacted with the probes. Thus by measuring the position of the caustic at different times after the probes have been mixed with the targets it is possible to obtain information about the reaction kinetics.

The detection method of the invention is suitable for detecting bending of prior art cantilever-type devices but conveniently can be used to detect bending of free-standing encoded carriers which comprise a code region having a code and a reaction region separate from said code region.

The above methods may be extended to a plurality of probes where a plurality of different types of reaction region are provided on a plurality of encoded carriers having different codes, such that each type of reaction region is attached to carriers having the same code. The carriers can then be introduced to the target molecules and the presence and/or position of the caustic can be determined by illumination with radiation.

The reaction region on the carrier may comprise a reactive material that expands or contracts upon reaction with target molecules. For example, a shape changing polymer matrix may be used.

As an alternative the reaction region may comprise probe molecules that react with the target molecules. For example, if the target molecules are antibody molecules then the carrier surface in the reaction region could be functionalised with antigen molecules.

Preferably, the illuminating radiation is collimated.

It has been found that, at low values of carrier bending (i.e. large radius of carrier curvature), small changes in the amount of carrier deflection will produce large changes in the position of the caustic feature. Therefore, preferably, the carrier is, prior to reaction with the target molecules, generally planar. Any subsequent deflection/bending of the carrier will thereby result in large changes in the position of the caustic.

In any caustic resulting from a curved surface at least one caustic node will be present—a caustic node being a point where the radiation intensity along the caustic curve is at a local maximum. It should be noted that the terms "node" and "cusp" are considered as interchangeable.

It has been found that the displacement of the caustic node from the carrier is related in a predictable manner to the radius of curvature of the carrier. Therefore, preferably, in the second aspect of the present invention the feature of the caustic that is measured is the caustic node.

The position of the caustic may be simply obtained from any suitable imaging apparatus by first focussing on the carrier to obtain a first focal distance and then re-focussing on the caustic optical feature to obtain a second focal distance. The difference between the first and second focal distances equates to the displacement of the caustic feature relative to the carrier. It can therefore be seen that the distance z of the caustic node from the carrier (as shown in FIG. 4) that is measured is along the imaging line of sight. Note: the location of a caustic node can be determined either by locating the position (relative to the carrier) at which the radiation intensity at the centre of the node being measured reaches a maximum or by determining when the physical size of the node reaches a minimum.

The above method can therefore advantageously comprise the further step of determining the radius of curvature of the carrier in order to determine information about the reaction in question.

Advantageously, the carrier can further comprise a diffraction grating. Where such a carrier is illuminated by white light the different wavelength components of the white light will be diffracted at different angles. A number of caustic nodes will therefore be measurable and the position and relative separation of these nodes can also be used to monitor the reaction.

For a carrier comprising a grating a central, zero-order, node will be present. If white light is used to illuminate the carrier then this zero order node will also be white. A series of higher order nodes (e.g. $1^{st}$ order, second order etc.) will also be visible but for each order there will be a number of nodes corresponding to the constituent wavelengths of the illuminating white light.

For any given grating, the lateral separation of the various caustic nodes will be dependent on the distance z. Therefore there will also be a relationship between the lateral node separation (i.e. the separation in a plane substantially perpendicular to the imaging line of sight) and the radius of curvature. The radius of curvature can therefore be determined by measuring the lateral node separation between nodes in a given order (or between nodes in different orders) or by measuring the separation of higher order nodes from the central zero order node. Thus, the radius of curvature can either be determined directly from the node separation or the node separation can be used as a check of the radius of curvature derived from the distance z.

It should be noted that in practice control carriers, i.e. carriers having no surface functionalisation or reactive layers, should be included within the detection methods in order to determine between temperature of pH induced carrier bending and changes due to binding or other target specific events.

In a third aspect of the present invention there is provided an encoded carrier for detecting target molecules comprising a code region having a code and a reaction region separate from said code region wherein in use the carrier is arranged to flex.

The carrier may be arranged to flex from an initially substantially flat profile to a curved profile, from an initially curved profile to a substantially flat profile or may be arranged to increase in its amount of curvature. It should be noted that the carrier may flex through the flat position e.g. from a "convex" to a "concave" profile.

Such a free standing carrier can be analysed according to the methods of the present invention to determine whether the reaction has taken place and also reaction kinetics. An advantage of the third aspect of the present invention is that further species of target molecules may be analysed by the simple step of including further carriers sensitive to such further molecules in the reaction. No re-design or alteration of existing carriers is required as would be the case for a cantilever device of the prior art.

As noted above, the carrier may advantageously include a diffraction grating and may furthermore initially be generally planar in construction. The carrier may also be reactive on both surfaces. For such double sided carriers the opposing faces could be sensitive to different target molecules.

A carrier can conveniently comprise a dielectric layer and a metal layer. The metal layer may be selected from Al, Au, Cr, Co, Cu, In, Fe, Pb, Mg, Mn, Mo, Ni, nichrome, Nb, Pd, Pt, Se, Ag, Ta, Te, Sn, Ti, W, Zn, and Zr.

The dielectric layer may be selected from $Al_2O_3$, $BaTiO_3$, CdO, CdSe, CdS, $CeO_2$, Germanium oxide, indium oxide, $Fe_2O_3$, $Fe_3O_4$, $MgF_2$, $SiO_2$, SiO (or any intermediate stoichiometric ratio of Si and O between SiO and $SiO_2$), $Si_3N_4$, tin oxide, $TiO_2$, TiO, ZnSe, ZnS and $Y_2O_3$.

The carrier may also be made of other (at least slightly reflective) materials.

Selective binding of the target molecules to the carrier surface will cause bending by electrostatic and steric effects.

Alternatively, a responsive polymer surface layer could be used to deform the carrier when triggered by a specific activating agent.

Preferably, the carrier is less than 1000 μm by 1000 μm, more preferably less than 400 μm by 400 μm, and more preferably still the carrier is less than 100 μm by 100 μm.

The code region on the carrier may comprise a bar code region, an alpha-numeric code or any other suitable geometrical pattern.

In a fourth aspect of the present invention there is provided a method of determining the position of a caustic optical feature resulting from an encoded carrier according to the third aspect of the present invention when used in a method according to either the first or second aspects of the present invention comprising the steps of imaging the carrier in an imaging apparatus to obtain a first focal distance imaging the caustic optical feature in the imaging apparatus to obtain a second focal distance deriving the separation of the caustic feature from the carrier by determining the distance between the first and second focal distances.

It should be noted that the second focus need not necessarily be closer to the imaging apparatus than the first focus. In such instances, a "virtual" focus can be observed further away from the imaging apparatus than the first focus (i.e. behind the carrier).

The terms "probe" or "probe molecules" have been used to refer to the molecules which are attached to the encoded carrier. The terms "target" or "target molecules" have been used to refer to the molecule which is to be reacted with the molecules already attached to the encoded carriers. The probes and targets may be chosen from a number of different types of molecules for example, antibodies, antigens, enzymes, toxins, proteins, genes etc.

Embodiments of the present invention will now be described, by way of example only, with respect to the following figures in which:

FIG. 1 is a schematic of an encoded carrier in accordance with an embodiment of the present invention prior to reaction of the carrier with a target species FIG. 2 is a schematic of the carrier of FIG. 1 following reaction with the target species.

FIG. 8 shows images of an encoded carrier of the general type shown in FIG. 7 which show caustic features as measured in the methods according to the present invention;

FIGS. 10*a* and 10*b* show images of examples of carriers according to the present invention and their corresponding catacaustic nodes.

Figure 11:
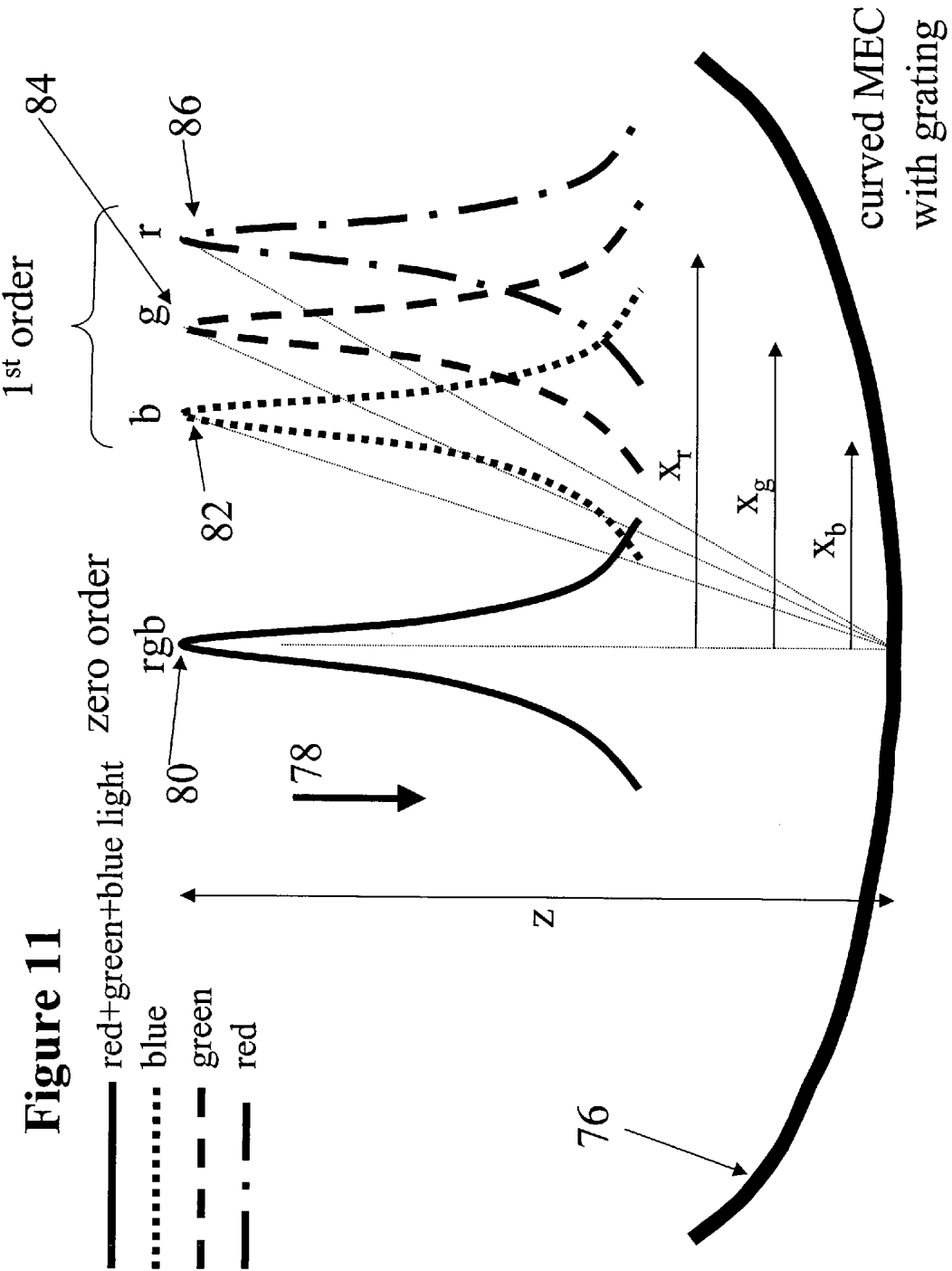
Figure 12:
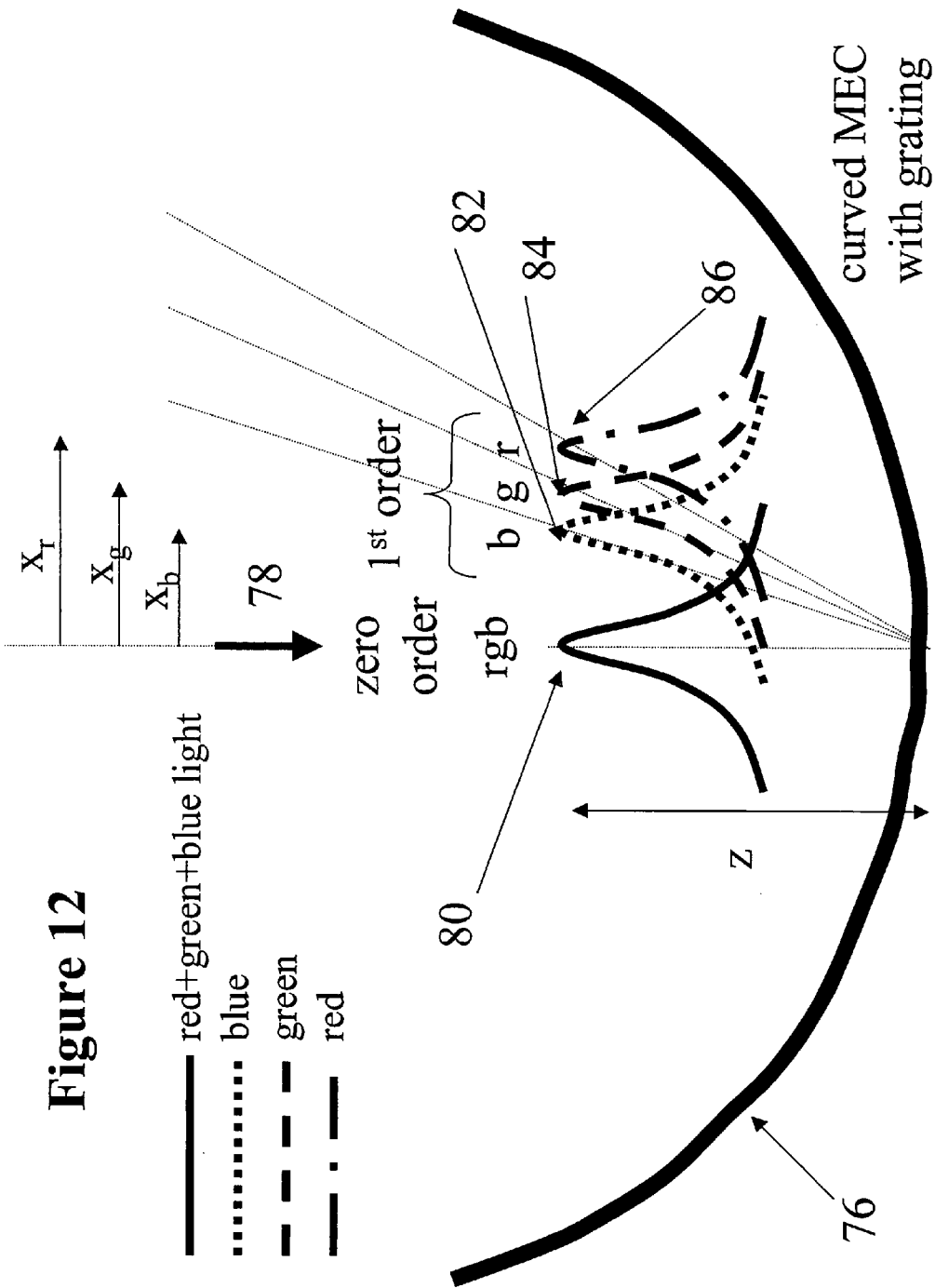
Figure 13A:
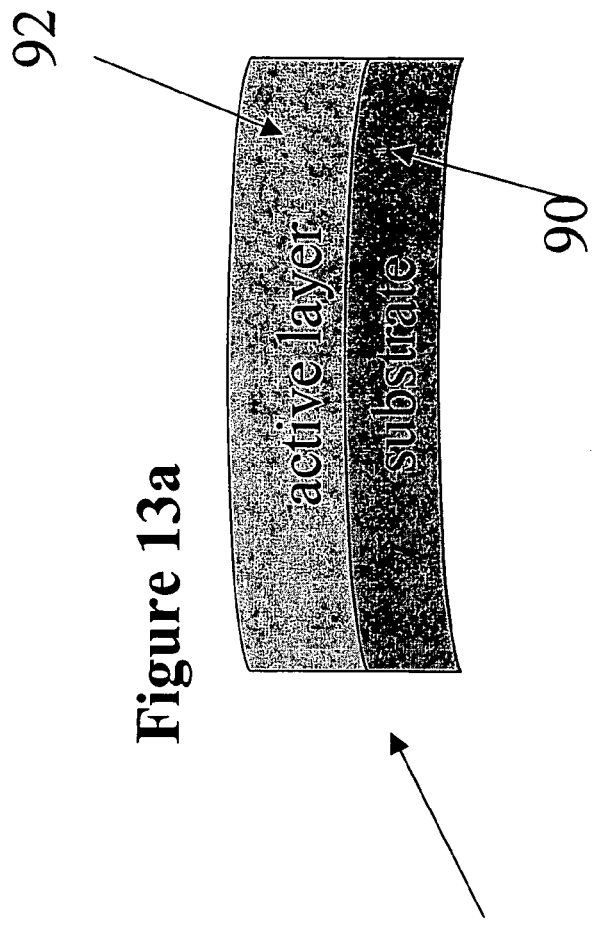
Figure 13B:
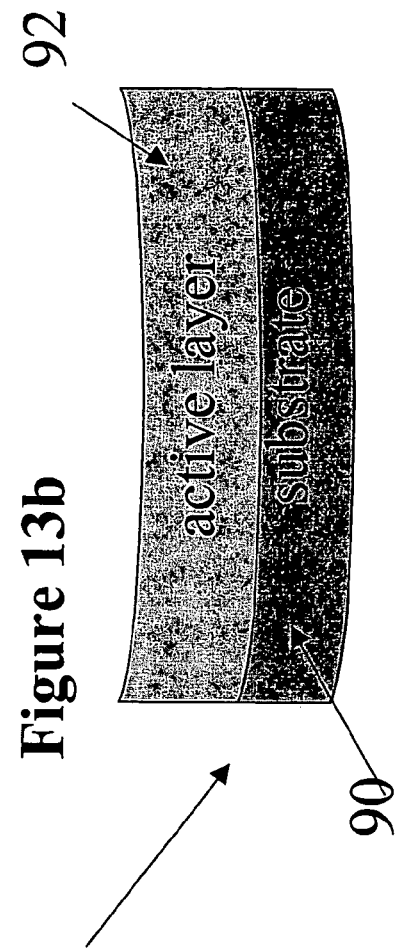
Figure 13:
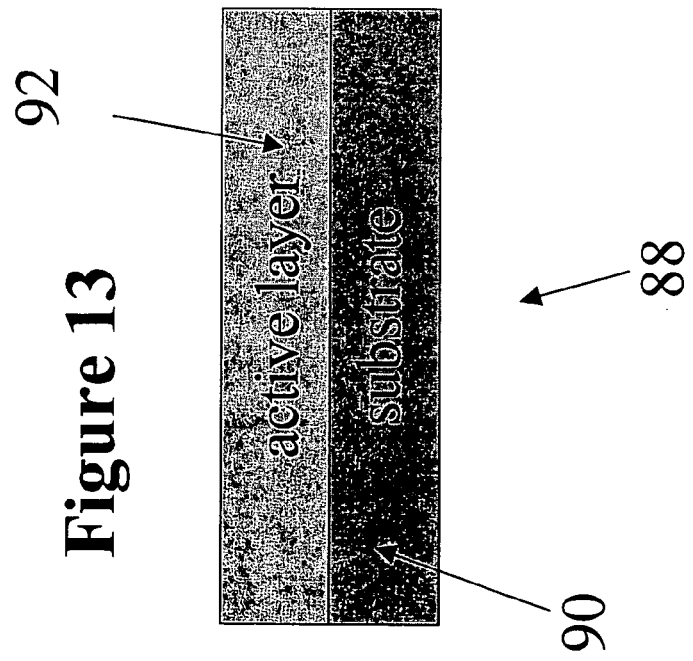

FIG. 11 schematically illustrates the effect of a diffraction grating on a carrier illuminated with white light (red+blue+green components) for a large radius of carrier curvature FIG. 12 schematically illustrates the effect of a diffraction grating on a carrier illuminated with white light (red+blue+green components) for a small radius of carrier curvature FIGS. 13, 13*a* and 13*b* show a carrier comprising a substrate and a reactive layer.

Figure 14:
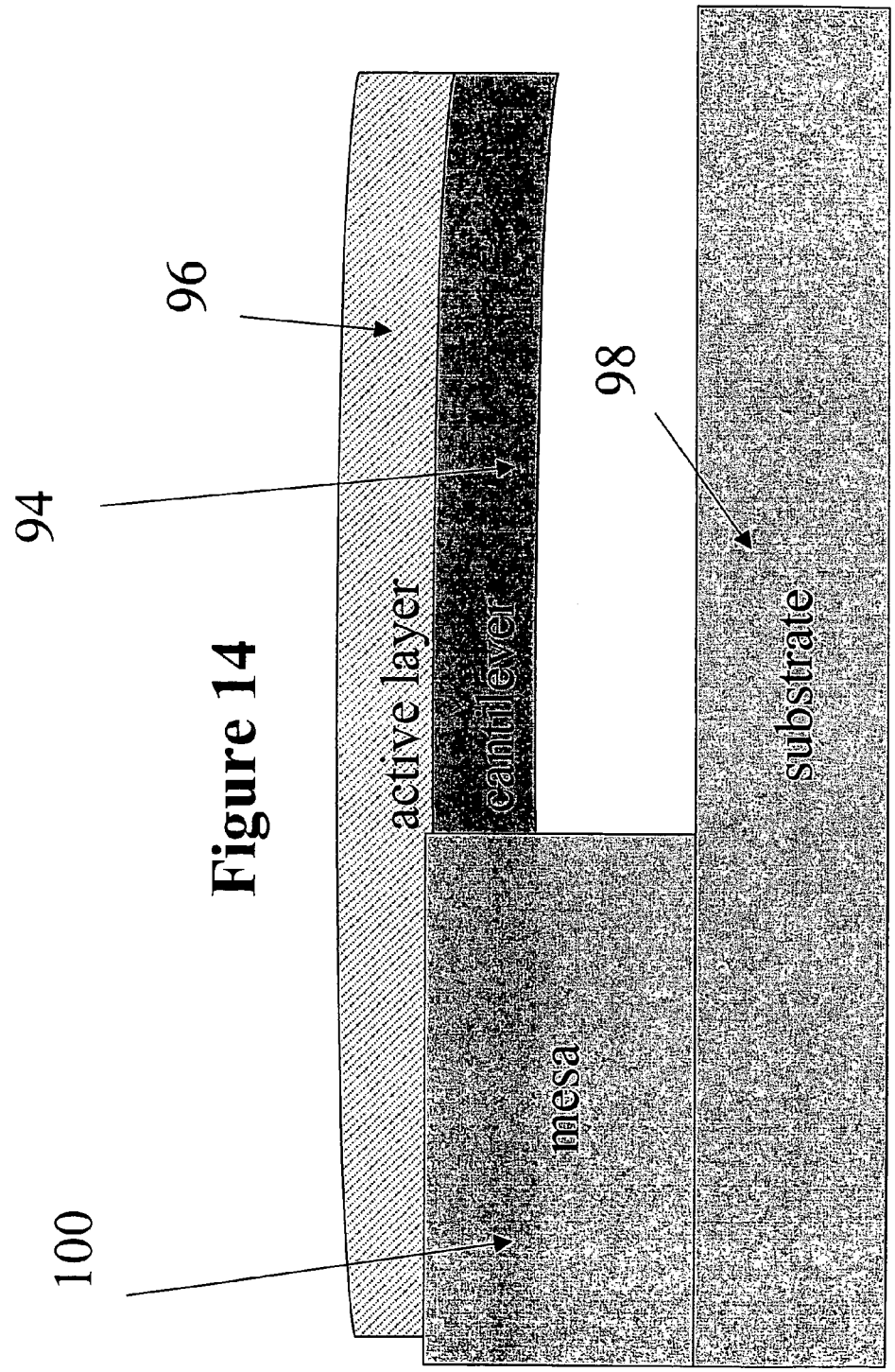

FIG. 14 shows a cantilever type device comprising a substrate and a reactive layer.

FIG. 1 shows an embodiment of a carrier of the present invention wherein a carrier 1 of substantially flat profile has an inert surface 3 and a functionalised surface 5. The functionalised surface is arranged to be capable of reacting with a target species. For example, the surface 5 could comprise antigen molecules 7 suitable for reacting with a specific antibody molecule.

FIG. 2 shows the carrier of FIG. 1 following an antibody-antigen reaction (like numerals are used to denote like features). A series of antibody molecules 9 are bound to the antigen molecules 7 on the functionalised surface 5. The carrier 1 has bent to accommodate the binding of the larger target molecules.

Figure 3:
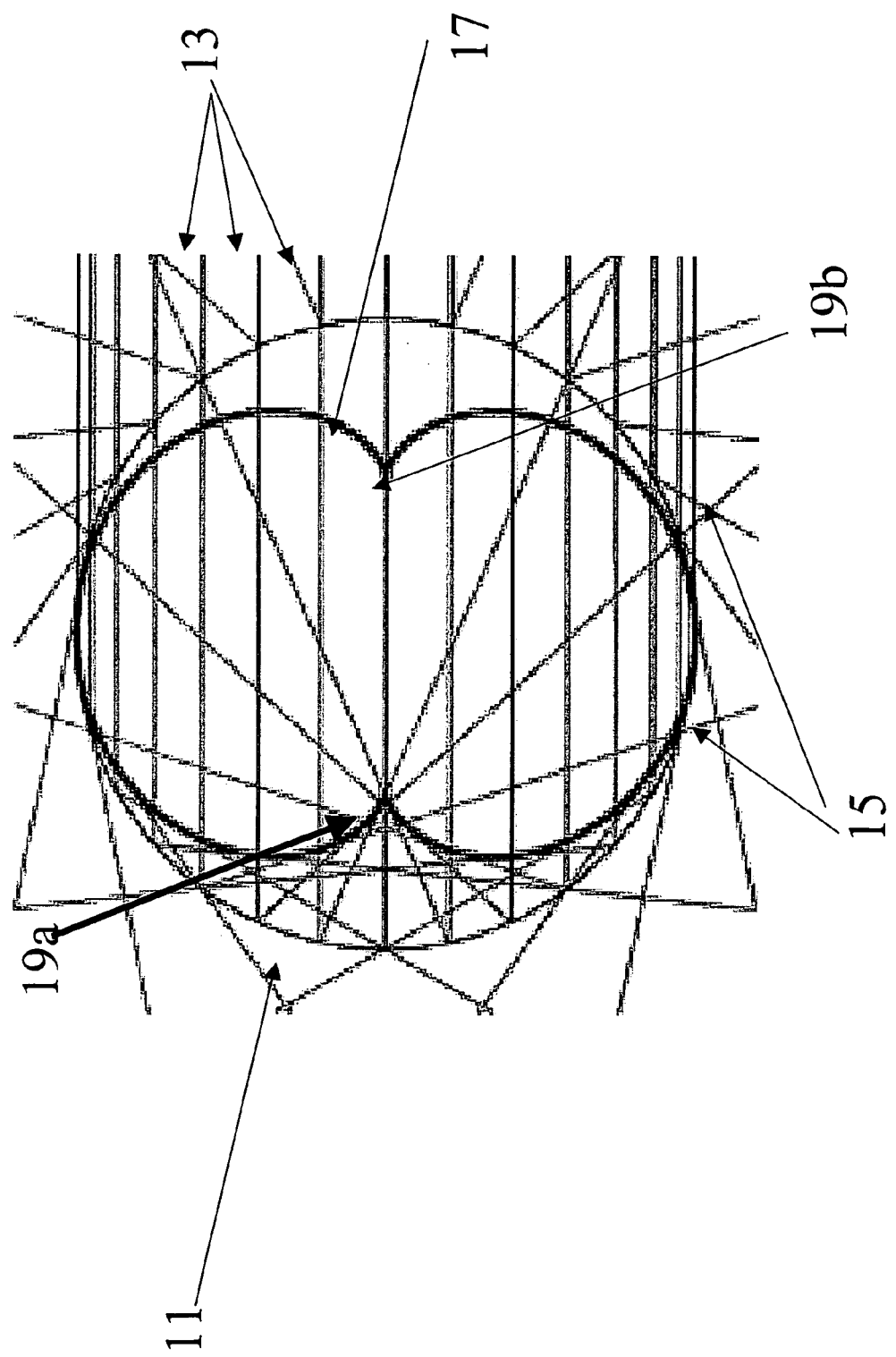
FIG. 3 shows the position of a caustic observed when radiation illuminates a circle.

FIG. 3 illustrates how a caustic curve forms within a circle. A circle 11 is illuminated by a light source (not shown). Ray paths 13 are shown for the illuminating radiation and it can be seen that the source is effectively located at infinity. The inside surface of the circle 11 is reflective and the ray paths 15 for the illuminating radiation upon reflection are shown. The caustic curve 17 produced by this arrangement is shown.

As noted previously, a caustic is generally defined as a curve to which the ray of light, reflected or refracted by another curve, are tangents, the reflecting or refracting curve and the luminous point being in one plane. In this instance the caustic curve 17 is in the form of a double arc.

The arrangement shown in FIG. 3 approximates to the case where sunlight falls on a coffee cup. In such a situation a double arc of reflected sunlight is often seen on the surface of the liquid in the cup.

The points 19*a* and 19*b* are caustic nodes where the intensity of the observed radiation will be at a local maximum. It is the position of the caustic node resulting from radiation illuminating the curved carrier surface of FIG. 2 that is measured in the method of the present invention.

In FIG. 3 the illuminating radiation is coming from the right hand side of the Figure. Therefore the left hand side of the circle is producing a "real" node at point 19*a* and the right hand side of the circle is producing a "virtual" node at point 19*b* (since the node 19*b* is located on the opposite side of the circle (i.e. "carrier") to the radiation source).

Figure 4:
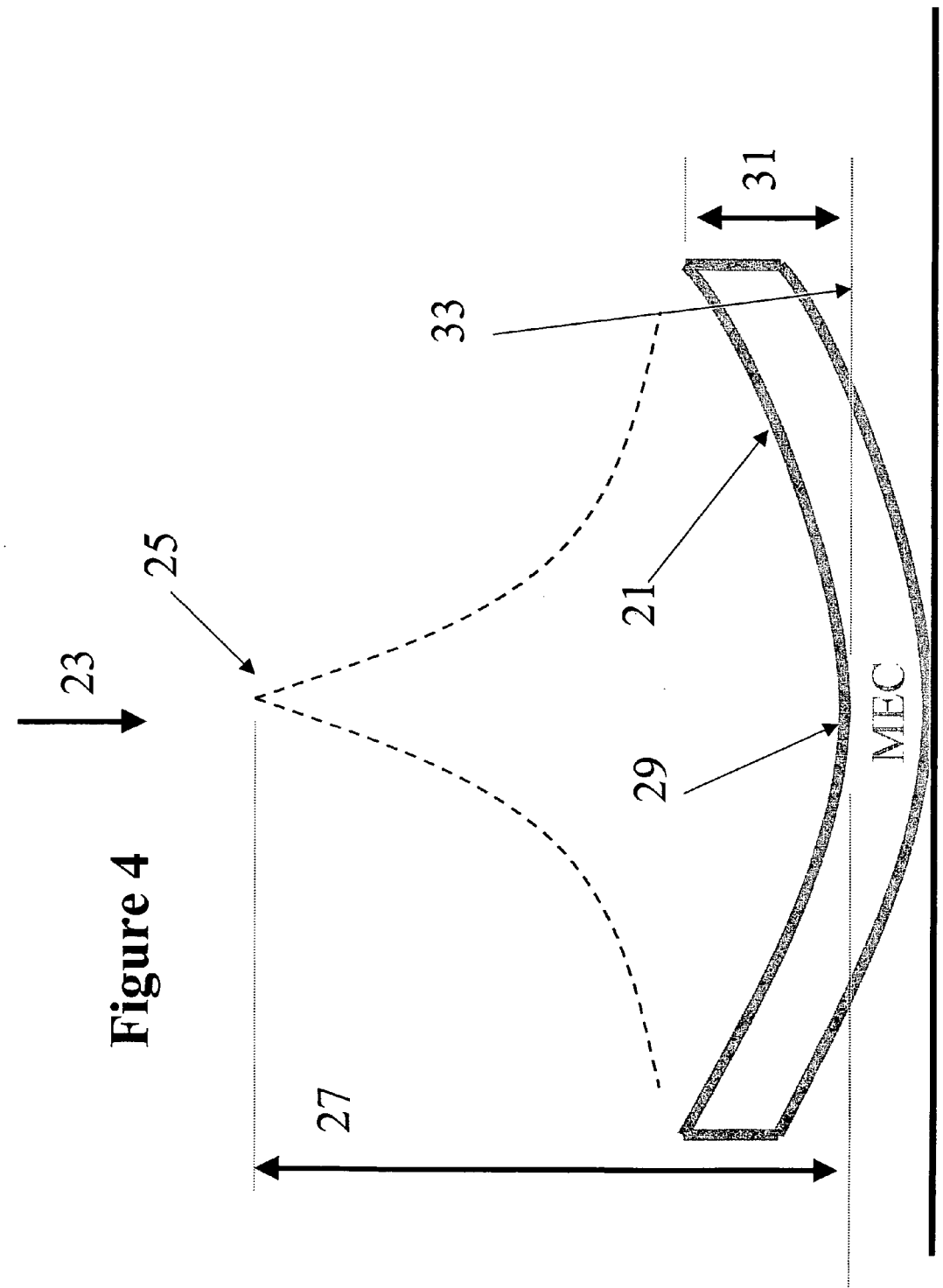
FIG. 4 shows a schematic of an encoded carrier following interaction with a target species indicating various features of the caustic.

FIG. 4 shows a further schematic for a curved carrier. In this instance a carrier 21 is illuminated by radiation from a source (not shown) in the direction of the arrow 23. Reflected light forms a catacaustic with a node point 25 as shown. The catacaustic node displacement 27 equates to the distance between the catacaustic node and the front face of the carrier 21. The node displacement 31 is a measured term and can be used to derive the displacement of the centre of the carrier 29 from the initial horizontal starting configuration 33.

Figure 5:
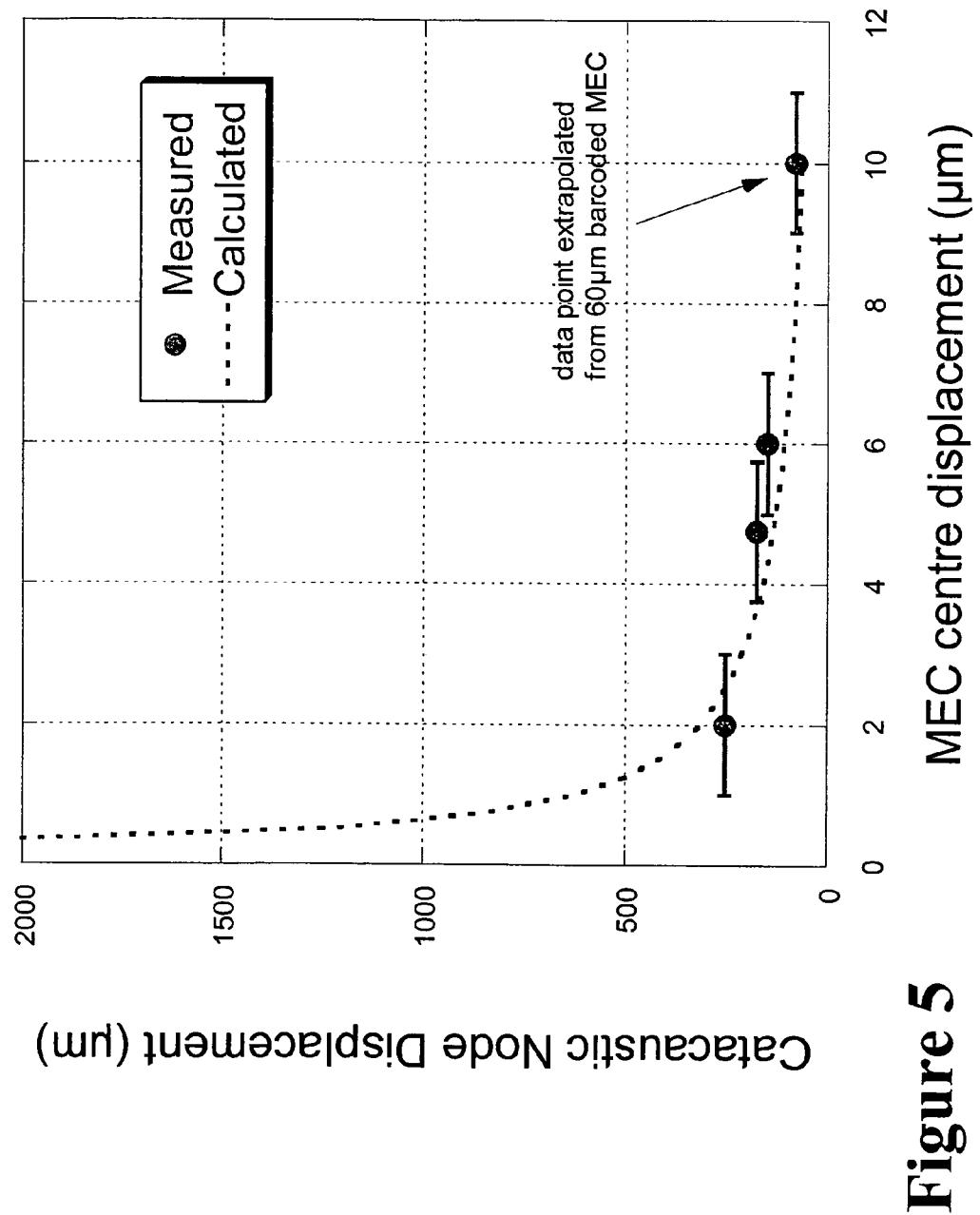
FIG. 5 shows graph of caustic node displacement versus carrier centre displacement

FIG. 5 shows the relationship between the centre displacement of the carrier and the caustic node displacement. It can be seen that measuring the position of the caustic node allows the displacement of the carrier to be determined. This in turn allows the radius of curvature of the carrier to be calculated.

Figure 6:
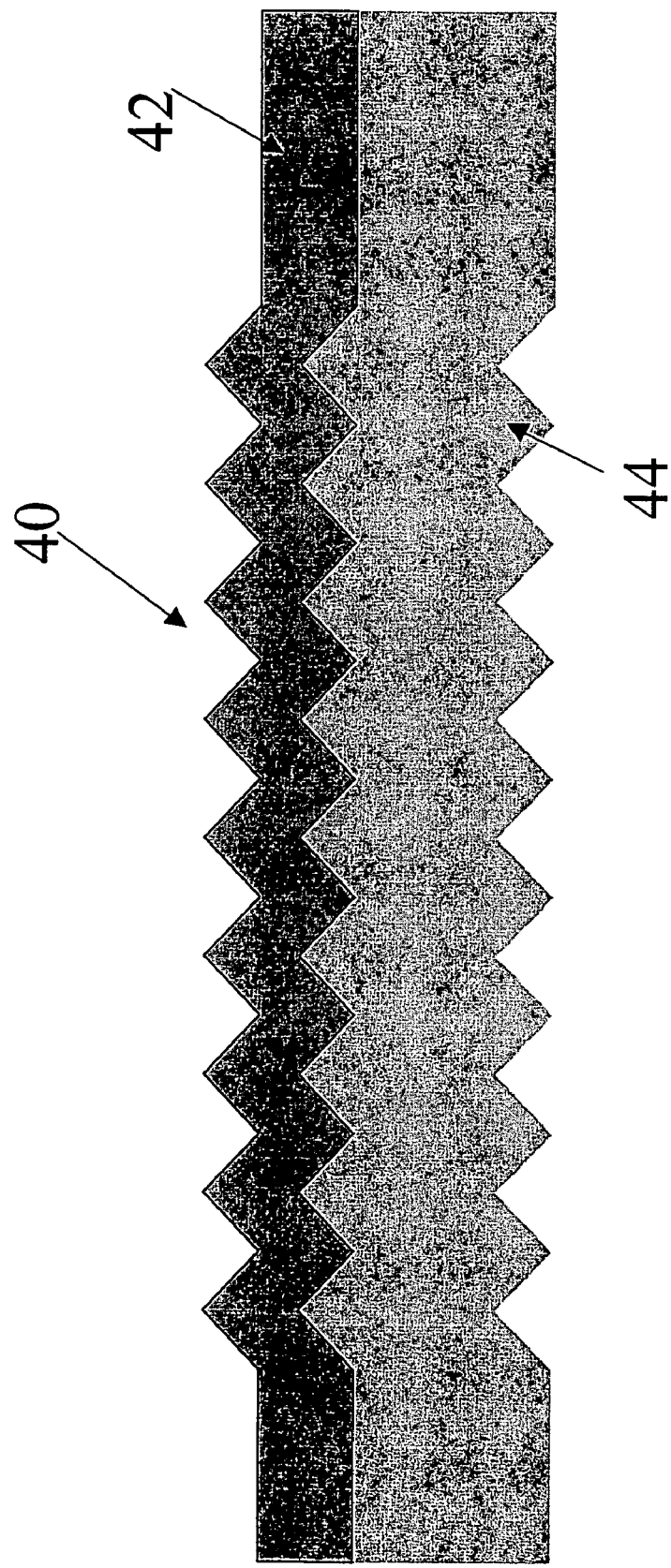
FIG. 6 shows a schematic cross section of a reaction region of an encoded carrier in accordance with the present invention.

FIG. 6 is a schematic cross section of an example of the reaction region of a carrier which additionally comprises a diffraction grating. The reaction region 40 comprises two corrugated layers 42 and 44. In this particular example, the upper corrugated layer 42 is a metal layer and the lower corrugated layer 44 is a dielectric layer.

Although the metal layer 42 is shown as the upper layer, either the dielectric or the metal layer can be used as the uppermost layer in the structure. Typically, the layer which will adhere to the target species will be chosen as the uppermost layer.

Figure 7:
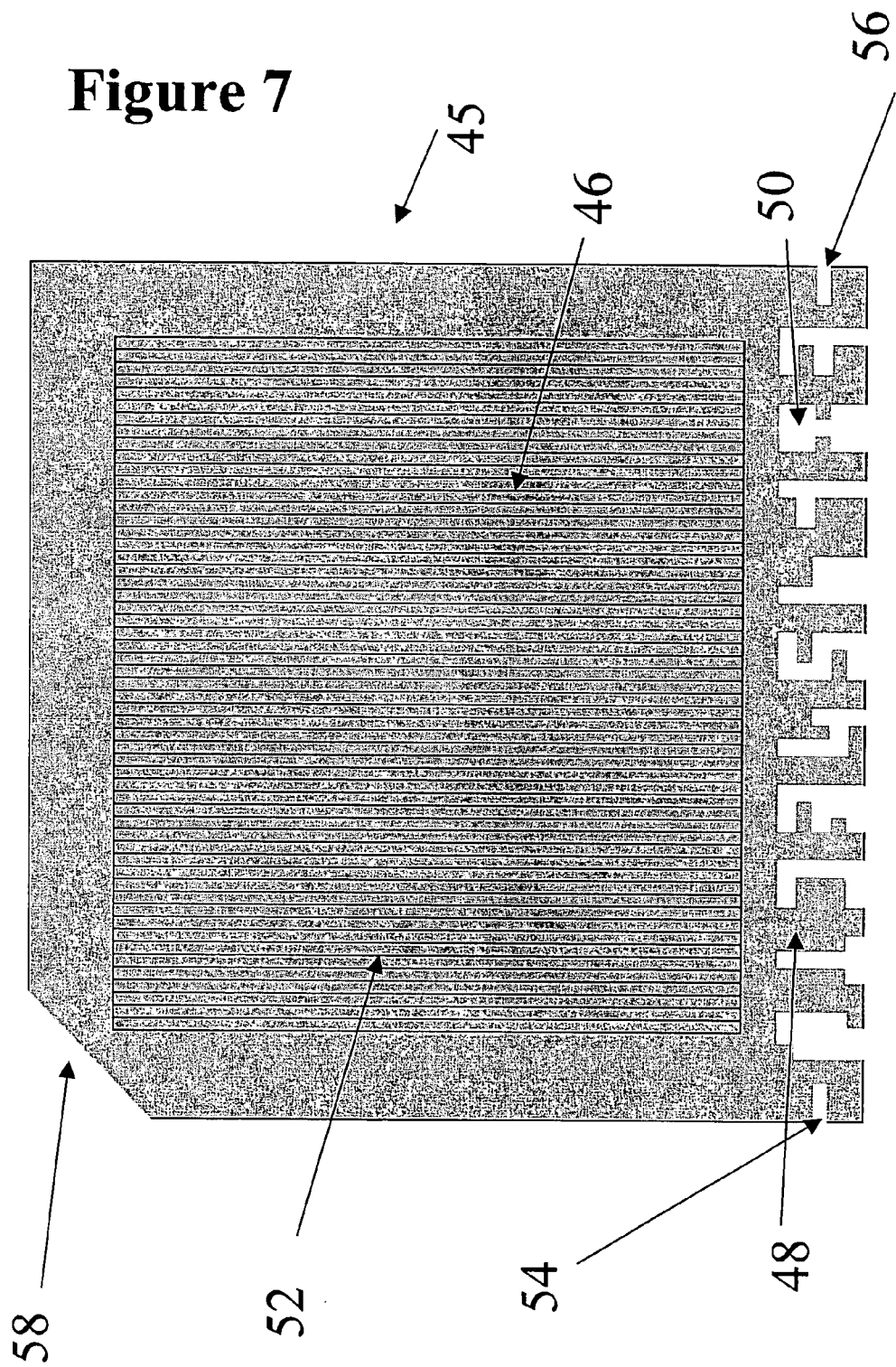
FIG. 7 shows an encoded carrier having a corrugated diffraction grating and an alphanumeric code in accordance with a preferred embodiment of the present invention

FIG. 7 illustrates an encoded carrier 45 in accordance with an embodiment of the present invention. The encoded carrier has a reaction region 46 and a coding region 48 comprising a code 50. The reaction region 46 comprises a diffraction grating 52. The grating may comprise a series of corrugations, changes in thickness in the reaction region or slots through the reaction region. The grating could also be circular. As an alternative to a one dimensional grating, a two dimensional array of protrusions from, or pits in, the surface of the reaction region may be used.

In the embodiment shown in the Figure, the diffraction grating comprises laminated corrugated layers (similar to those depicted in FIG. 6).

The code 50 is an alphanumeric code and each character is uniquely identifiable regardless of whether the code is read from above or below the plane of the carrier 45. Indents 54, 56 are provided on either side of the code region 48 indicating the middle line of the code 50. As mentioned above, alternatives to an alpha-numeric code would be a bar code or a geometrical pattern.

Corner 58 of encoded carrier 45 has been removed so that the orientation of the carrier can be determined. Confirmation of the orientation of the carrier 45 is necessary in order to correctly measure the reaction area since the orientation of the diffraction grating 52 with respect to the imaging apparatus should be the same for all encoded carriers 45. The orientation of the carrier 45 may also be useful for reading the code 50.

Typically, the encoded carrier 45 will be 50 to 100 µm square. Each of the characters of the bar code will typically have a length between 5 and 10 µm. The typical width of a code feature (e.g. a line in the bar code example or a number or letter in the alpha-numeric example) will be 1-2 µm.

In use, probes will be attached to reaction region 46. The molecules may be attached using a number of methods, but will preferably be attached by placing the encoded carriers in a solution of probes.

The encoded carriers 45 will then be introduced to molecules of a different type, "target molecules". Typically, this will again be performed by placing the encoded carriers with the probes in a solution or suspension of the target molecules.

If the probes attached to reaction area 46 react with the targets, the characteristics of the reaction area will change as described with reference to FIGS. 1 to 5.

In practice, a plurality of encoded carriers 45 will be prepared, by attaching a first type of probes to a first plurality of encoded carriers having the same "first" code, a second type of probes (different to the first type of probes) to a second plurality of encoded carriers having the same "second" code. The second code is different to the first code. Further encoded carriers with third, fourth, fifth etc codes and types of probes will be prepared. The reaction region 46 for each different type of encoded carrier having a different probe will be analysed as explained with reference to FIGS. 4 and 5 to determine the caustic node position.

In use, the different types of encoded carriers 45 are introduced into a solution containing the target molecules. The encoded carriers may then be removed from the solution and measured. Alternatively, the carriers may be read while in the solution. Each type of encoded carrier may be determined from its code. A measurement can then be performed to determine if the probes on the carrier have reacted with the target molecule.

The encoded carriers 45 may also be used to monitor the progress of a reaction between a molecule attached to the carrier and a target molecule. At the start of the reaction, only a few of the probes attached to the encoded carrier will react with target molecules. As the reaction progresses, more and more of the probes will react with the target molecules allowing the reaction kinetics to be studied.

FIGS. 8*a* to 8*c* show images taken of an actual encoded carrier. From FIG. 8*a* it can be seen that the carrier is of generally the same form as the carrier described in relation to FIG. 7. Like numerals have been used to denote like features between FIGS. 7 and 8. The image of the carrier 45 in FIG. 8*a* is shown in focus under a ×50 objective lens. In this example the code 50 used is numeric. The illuminating radiation comprises multiple wavelengths.

FIG. 8*b* shows that as the image of the carrier 45 is defocused catacaustic nodes 60 begin to appear. The image shown in FIG. 8*b* is shown under a ×20 objective lens. The multiple node pattern results from the action of the multiple frequencies in the illuminating radiation acting upon the grating 52 of the carrier 45.

As the image of FIG. 8*b* is defocused further the catacaustic nodes 60 come into focus as shown in FIG. 8*c*.

The catacaustic node displacement can be derived from such images. The carrier is initially imaged so that it is in focus and then the image is defocused until the catacaustic nodes come into focus. The change of position of the focus required can be related to the catacaustic node displacement and then a graph similar to the one shown in FIG. 5 can be used to determine the deflection of the centre of the carrier (and therefore the radius of curvature).

Figures 9, 9A, 9B:
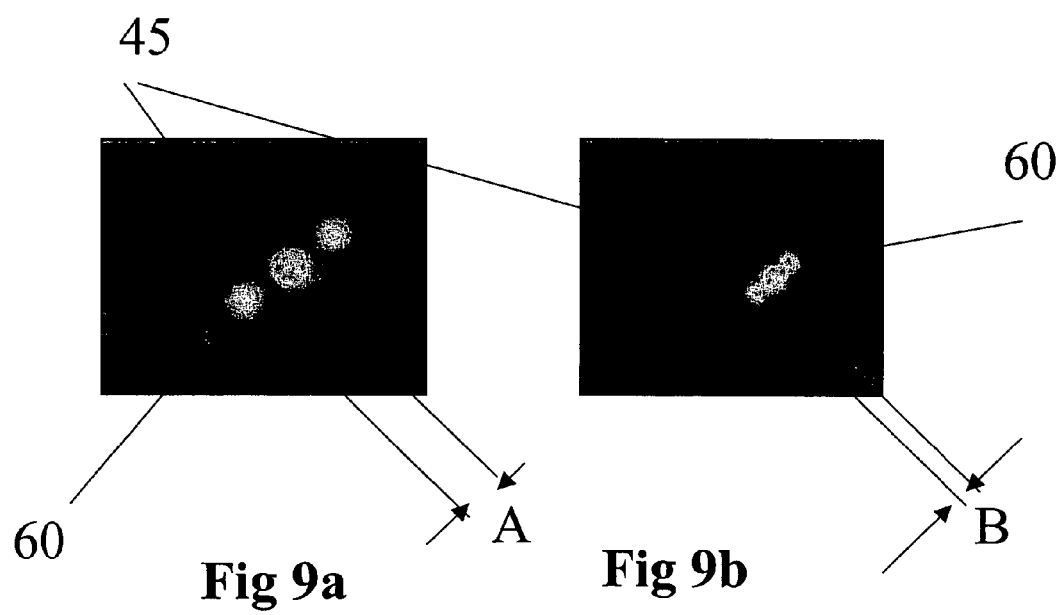
FIG. 9 shows the effect of the radius of curvature of the carrier on the measured caustic node separation.

FIG. 9 shows the effect of the radius of curvature on the observed node pattern. The carrier shown in FIG. 9*a* has a larger radius of curvature than the carrier in FIG. 9*b*.

Both carriers exhibit similar node patterns but it can be seen that the node spacings (labelled A and B) are different. The node spacing can also be linked to the catacaustic displacement and therefore the radius of curvature and so provides an alternative method for calculating reaction characteristics.

Both carriers shown in FIGS. 9*a* and 9*b* have gratings of 3.4 µm pitch and comprise a lower layer of $SiO_2$ and an upper layer of Au.

FIG. 10*a* shows four carriers according to the present invention. Carriers 62, 64 and 66 are all same side up. Carrier 68 is opposite side up (this can be determined by the position of the cut-off corner 70 relative to the other three carriers).

FIG. 10*b* shows the carriers of FIG. 10*a* with the catacaustic nodes in focus. It should be noted that the nodes 72, 74 are elongated due to the nature of the grating and the nature of the illumination. It should also be noted that since carrier 68 is curved in the opposite sense to the other carriers its nodes are out of focus. The nodes 74 relating to this carrier 68 could be imaged as "virtual" nodes by focusing below the plane of the paper.

FIGS. 11 and 12 show the effects of a grating on the observed caustic. In FIG. 11 a carrier 76 with a large radius of curvature (i.e. a low degree of carrier bending) is shown. White light (comprising a red, blue and green component) illuminates the carrier in the direction 78 from a source (not shown). The carrier additionally comprises a grating. Note: as an alternative the illuminating radiation could comprise red, green and blue components only so that pure colour nodes are observed.

Light reflected by the carrier forms a catacaustic node 80 at a distance z from the centre of the carrier. The diffraction grating has the effect of splitting the white light into its constituent wavelengths such that further catacaustic nodes 82, 84, 86 are created corresponding to blue, green and red light respectively (Note: in reality further nodes would also be present to the left of the central node but these have been omitted here for clarity). These nodes are located at distances Xr (for the red component), xg (for the green component) and Xb (for the blue component) from the centre of the carrier since each wavelength component is diffracted through a different angle. The central node 80 appears as white light and corresponds to the zero order of the grating. The nodes 82, 84, 86 correspond to the first order of the grating. Higher order nodes would also be present at larger values of x.

FIG. 12 shows a similar arrangement to FIG. 11 (and like numerals have been used to denote like features). In this case however the carrier 76 has a smaller radius of curvature (i.e. the amount of deflection of the carrier from the horizontal is greater than in FIG. 11). The smaller radius of curvature results in the catacaustic zero order node being closer to the carrier than the example shown in FIG. 11. The further first order catacaustic nodes 82, 84, 86 are therefore more closely spaced than in FIG. 11, i.e. $x_r$, $x_g$ and $x_b$ are smaller.

From FIGS. 11 and 12 it can therefore be seen that as z decreases the distances $x_r$, $x_g$ and $x_b$ decrease as well. Therefore measuring these x distances provides a convenient technique for checking the value of z and also a further manner in which to calculate the radius of carrier curvature (since the grating pitch will be known).

FIG. 13 shows an alternative arrangement for a carrier compared to the functionalised surface shown in FIGS. 1 and 2. In this case the carrier 88 comprises a reflective substrate 90 in contact with a responsive polymer layer 92. In use target molecules enter the polymer matrix resulting either in expansion of the active layer 90 (FIG. 13a) or contraction of the active layer 90 (FIG. 13b). In either case, changes in the active layer 90 distort the carrier 88 so that the carrier will exhibit caustic effects.

FIG. 14 shows an arrangement whereby the methods of the present invention can be used to analyse a cantilever type structure instead of a free-standing carrier. In this case a cantilever 94 is covered with either a monolayer 96 of a particular molecular species (i.e. a functionalising probe layer) or a thicker layer 96 of an active material such as a shape changing polymer matrix. The cantilever 94 is connected to a substrate 98 via a mesa 100. Exposure to the target species will deflect the cantilever and illumination of the set-up will result in the formation of caustics as before which can be analysed in accordance to the methods of the present invention.

The invention claimed is:

1. An encoded carrier device for detecting target molecules, comprising:
   a carrier capable of flexing and comprising a code region having a code and a reaction region separate from said code region,
   said reaction region comprising a reflective layer and a diffraction grating,
   wherein said reaction region comprises a functionalized surface comprising a plurality of probe molecules which are smaller than target molecules and which are capable of reacting with the larger target molecules to produce flexing of the carrier, and wherein flexing of the carrier is monitored by means of said reflective layer and said diffraction grating.

2. An encoded carrier device as claimed in claim 1 wherein the carrier has a substantially flat profile when no target molecules have reacted with said functionalized surface.

3. An encoded carrier device as claimed in claim 1 wherein the carrier has a curved profile when no target molecules have reacted with said functionalized surface.

4. An encoded carrier device according to claim 1, wherein said carrier comprises a dielectric layer and said reflective layer comprises a metal layer.

5. An encoded carrier device according claim 1, wherein the carrier comprises two separate reaction regions on opposing faces of the carrier.

6. An encoded carrier device according to claim 1, wherein the reaction region comprises a responsive polymer that expands or contracts upon reaction with target molecules.

7. An encoded carrier device according to claim 1, wherein the carrier is less than 400 μm by 400 μm.

8. An encoded carrier device as claimed in claim 1, wherein the reflective layer is a metal layer.

9. An encoded carrier device according to claim 8, wherein the metal is selected from Al, Au, Cr, Co, Cu, In, Fe, Pb, Mg, Mn, Mo, Ni, nichrome, Nb, Pd, Pt, Se, Ag, Ta, Te, Sn, Ti, W, Zn, and Zr.

10. An encoded carrier device according to claim 9, wherein the metal is Gold.

* * * * *